United States Patent
Cuscuna et al.

(10) Patent No.: US 12,295,786 B2
(45) Date of Patent: May 13, 2025

(54) PULL-CABLE MANAGEMENT FOR STEERABLE CATHETER

(71) Applicant: KONINKLIJKE PHILIPS N.V., Eindhoven (NL)

(72) Inventors: Dino Francesco Cuscuna, Reading, MA (US); Edward Chan, Brookline, MA (US); John Bench Caswell, Manchester, NH (US); Brian Michael Bishop, Pelham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 471 days.

(21) Appl. No.: 17/611,257

(22) PCT Filed: May 20, 2020

(86) PCT No.: PCT/EP2020/064017
§ 371 (c)(1),
(2) Date: Nov. 15, 2021

(87) PCT Pub. No.: WO2020/234328
PCT Pub. Date: Nov. 26, 2020

(65) Prior Publication Data
US 2022/0225960 A1    Jul. 21, 2022

Related U.S. Application Data

(60) Provisional application No. 62/850,669, filed on May 21, 2019.

(51) Int. Cl.
*A61B 8/00*    (2006.01)
*A61B 8/12*    (2006.01)
(Continued)

(52) U.S. Cl.
CPC ............... *A61B 8/445* (2013.01); *A61B 8/12* (2013.01); *A61M 25/0032* (2013.01);
(Continued)

(58) Field of Classification Search
None
See application file for complete search history.

(56) References Cited

U.S. PATENT DOCUMENTS 3,799,152 A * 3/1974 Kim ..................... A61B 1/2733
                                                    600/162
7,235,089 B1    6/2007 Mcguckin
(Continued)

FOREIGN PATENT DOCUMENTS

EP    0605796 A2    7/1994
EP    0782836 A1    7/1997
(Continued)

OTHER PUBLICATIONS

International Search Report and Written Opinion of PCT/EP2020/064017, dated Aug. 14, 2020.

*Primary Examiner* — Katherine L Fernandez

(57) ABSTRACT

A steerable catheter comprises a transducer that is situated at a flexible distal end, and is coupled to the handle of the catheter via an insertion tube. The flexible distal end is controlled by a plurality of articulation pull-cables that extend from an articulation control device in the handle to the far end of the distal end, such that when one articulation pull-cable is pulled, and the opposing articulation pull-cable is slackened, the flexible distal end bends in the direction of the tensioned articulation pull-cable. To minimize pull-resistance over time, while still providing insertion-tube flexibility, inserts having pull-cable lumens are situated in
(Continued)

the insertion tube to isolate each articulation pull-cable from each other, and from other cables that couple the transducer to the handle.

11 Claims, 4 Drawing Sheets

(51) Int. Cl.
 *A61M 25/00* (2006.01)
 *A61M 25/01* (2006.01)
(52) U.S. Cl.
 CPC ............... *A61M 2025/0036* (2013.01); *A61M 2025/004* (2013.01); *A61M 25/0136* (2013.01); *A61M 25/0147* (2013.01)

(56) References Cited

U.S. PATENT DOCUMENTS

| | | | |
|---|---|---|---|
| 2003/0045778 A1 | 3/2003 | Ohline | |
| 2004/0122360 A1 | 6/2004 | Waldhauser | |
| 2006/0199999 A1* | 9/2006 | Ikeda | A61B 1/00149 600/141 |
| 2008/0161798 A1 | 7/2008 | Podmore | |
| 2008/0188868 A1 | 8/2008 | Weitzner | |
| 2013/0096572 A1 | 4/2013 | Donhowe | |
| 2013/0296781 A1 | 11/2013 | Tegg | |
| 2015/0094594 A1* | 4/2015 | Harhen | A61B 8/445 600/466 |
| 2016/0310701 A1 | 10/2016 | Pai | |

FOREIGN PATENT DOCUMENTS

| | | | | |
|---|---|---|---|---|
| EP | 1046406 A2 | 10/2000 | | |
| EP | 1072280 A2 | 1/2001 | | |
| EP | 2074928 A2 | 7/2009 | | |
| EP | 1737335 B1 * | 5/2013 | ......... | A61B 1/00071 |
| WO | 2005094665 A2 | 10/2005 | | |
| WO | WO-2008070556 A1 * | 6/2008 | ......... | A61B 1/00039 |
| WO | 2018060108 A1 | 4/2018 | | |

* cited by examiner

PULL-CABLE MANAGEMENT FOR STEERABLE CATHETER

CROSS-REFERENCE TO PRIOR APPLICATIONS

This application is the U.S. National Phase application under 35 U.S.C. § 371 of International Application No. PCT/EP2020/064017, filed on May 20, 2020, which claims the benefit of U.S. Provisional Patent Application No. 62/850,669, filed on May 21, 2019. These applications are hereby incorporated by reference herein.

FIELD OF THE INVENTION

This invention relates to the field of medical instruments, and in particular to a method and system for managing articulation pull-cables in a steerable catheter or other steerable instruments, such as endoscopes, gastroscopes, and transesophageal echocardiography (TEE) probes.

BACKGROUND OF THE INVENTION

Catheters are commonly used for situating elements within passages in a patient's body, to monitor particular biometrics, perform surgical procedures, administer medication, and so on. To navigate through the passages, steerable catheters having an articulating distal end have been developed.

FIGS. 1A-1C illustrate an example prior-art steerable catheter 100. The catheter 100 comprises a handle 110, an insertion tube 120, a flexible distal end 130, and a transducer 170. The transducer 170 acquires imaging data via ultrasound. Other devices may be substituted for transducer 170, these devices may receive biometrics of a patient and/or optical images of internal passages, or it may execute tasks such as making incisions, clearing blockages, administering medication, and so on. To perform these actions, the handle 110 is coupled to a medical-instrument controller (not shown) and is coupled to the transducer 170 via one or more transducer cables 150 within the insertion tube 120. In the example of the ultrasound transducer 170 above, the steerable catheter 100 may be an ultrasound probe, such as a transesophageal echocardiography (TEE) ultrasound probe, a transvaginal ultrasound probe, for use with an ultrasound system.

FIG. 1B illustrates the catheter 100 in a 'neutral' state wherein the flexible distal end 130 is not bent or twisted. The handle 110 includes an articulation controller 115 that is coupled to the flexible distal end 130 via articulation pull-cables 160a, 160b (collectively, articulation pull-cables 160) that extend through the insertion tube 120 to the flexible distal end 130.

As illustrated in cross-section 2A, these articulation pull-cables 160 are fixedly attached to a terminator 175 that is situated at the transducer-end of the flexible distal end 130, and can be selectively tensioned/pulled by the articulation controller 115.

As illustrated, the articulation pull-cables 160a, 160b are situated opposite each other at an outer perimeter area of the terminator 175. This enables two degrees of freedom for adjusting the orientation of the flexible distal end 130. In some embodiments, the flexible distal end 130 includes structural details that limit the bending of the flexible distal end 130 in the two opposite directions. When the upper cable 160b is pulled via the articulation controller 115, and the lower cable 160a is correspondingly slackened, via rotation 118 of the articulation controller 115, the tension causes the flexible distal end 130 to twist upwards, as illustrated in FIG. 1A. Reversing the rotation 119 on the articulation controller 115 causes the lower cable 160a to be pulled and the upper cable 160b to be slackened, causing the flexible distal end 130 to twist downward, as illustrated in FIG. 1C.

Although two articulation pull-cables 160a, 160b are illustrated, a steerable catheter may include a larger plurality of cables situated on the perimeter of the terminator 175 to provide additional degrees of freedom of movement. Typically, four articulation pull-cables are provided to provide horizontal and vertical bending of the flexible distal end 130.

In some embodiments, as illustrated in FIG. 3, pull-cable lumens 165 are provided through the flexible distal end 130 to provide a more uniform tension within the flexible distal end 130 as the articulation pull-cables 160 are tensioned/pulled.

For proper articulated steering, the flexible distal end 130 should be more flexible than the insertion tube 120, yet the insertion tube 120 must provide sufficient flexibility to minimize a patient's discomfort as the insertion tube 120 travels within the patient's internal vessels. Accordingly, a single lumen 190 is provided for routing the transducer cables 150 and articulation pull-cables 160, as illustrated in the cross-section of FIG. 2B, so that the flexibility of the insertion tube 120 may be determined primarily by the dimensions and composition of the material forming the cylindrical insertion tube 120. The single lumen 190 also facilitates the insertion/routing of the cables 150, 160 within the insertion tube 120. However, this structure-less lumen 190 introduces issues that affect the reliability and longevity of the steerable catheter 100, as detailed below.

SUMMARY OF THE INVENTION

An object of this invention is to provide a more robust catheter or similar elongated medical instrument device design by providing structure for cable routing within the insertion tube of a steerable catheter or (elongated) device without significantly affecting the flexibility of the insertion tube.

To better address one or more of these concerns, in an embodiment of this invention, the insertion tube may include a plurality of inserts that are spaced along the insertion tube from the handle to the distal end. Each insert of the plurality of inserts may include a plurality of lumens comprising one or more transducer-cable lumens and a plurality of pull-cable lumens, wherein the plurality of lumens isolate the transducer cable and each of the plurality of articulation pull-cables from each other.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions. The drawings are included for illustrative purposes and are not intended to limit the scope of the invention.

DETAILED DESCRIPTION

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

It is understood that the implementation of the following-described inventions in a catheter used in blood vessels is merely exemplary. The scope of the invention encompasses any steerable devices, such as elongated medical devices, including catheters, which are intended to be inserted into bodily vessels, canals, passageways and cavities, and which have steerable distal portions for use in imaging, medical procedures, placement of implants, removal of implants and the like.

Non limiting examples of other such medical devices falling within the scope of the invention are endoscopes, gastroscopes, transvaginal ultrasound probes, and transesophageal echocardiography (TEE) ultrasound probes. In an embodiment including a TEE, transducer 170 is of course an ultrasound transducer. The inventions as described below for use in the exemplary catheters may be readily implemented in these other elongated medical devices as well, and thus enjoy similar benefits and improvements over the prior art arrangements.

Figure 2A:
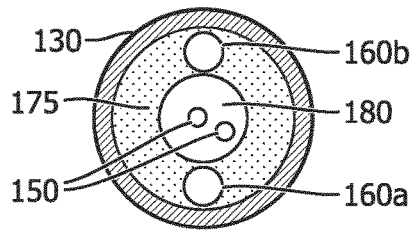
FIGS. 2A-2B illustrate example cross-sections of the prior art steerable catheter.
Figure 2B:
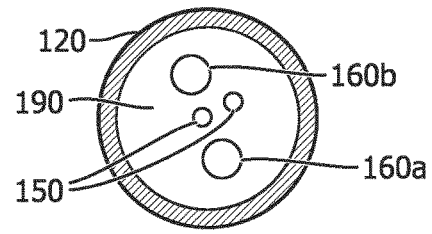
Figure 3:
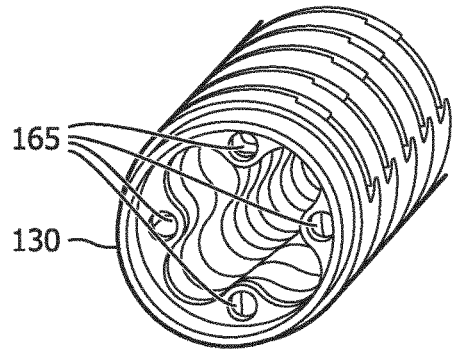
FIG. 3 illustrates an example prior art flexible distal end of a steerable catheter.

As mentioned above, the prior art catheter is prone to premature failure due to the structure-less lumen 190 of the insertion tube 120, illustrated in FIG. 2B. After repeated usage, the cables 150, 160 often become entangled with each other, causing an increased resistance in the tensioning and slackening of the articulation pull-cables 160. This increased resistance can often lead to a premature failure of the catheter 100 due to an inability to pull or slacken one of the articulation pull-cables 160. This increase of resistance can be lessened by encasing each articulation pull-cable 160 in a protective sleeve that is sized to enable the articulation pull-cable 160 to be pulled and slackened, and sufficiently rigid to withstand deformation by the other cables. However, such a protective shield on each articulation pull-cable 160 would significantly affect the overall flexibility of the insertion tube 120.

Figure 4:
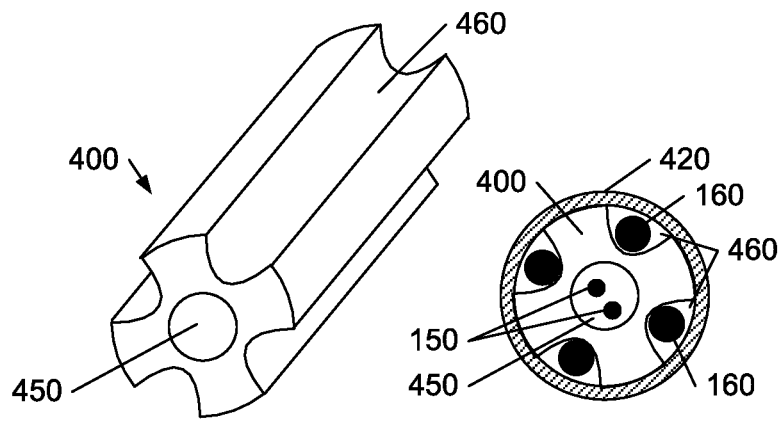
FIG. 4 illustrates an example insert for placement within an insertion tube.

FIG. 4 illustrates an example insert 400 that provides structure within an insertion tube 420. The example insert 400 includes a transducer lumen 450 through which one or more transducer cables 150 transit, and a plurality of pull-cable lumens 460, through which a plurality of steering cables 160 transit. As illustrated, the pull-cable lumen 460 is C-shaped, and forms an enclosed volume when situated within the insertion tube 420.

Figure 1A:
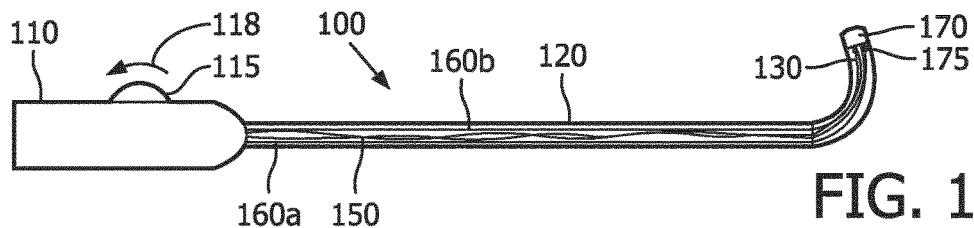
FIGS. 1A-1C illustrate an example prior art steerable catheter.
Figure 1B:
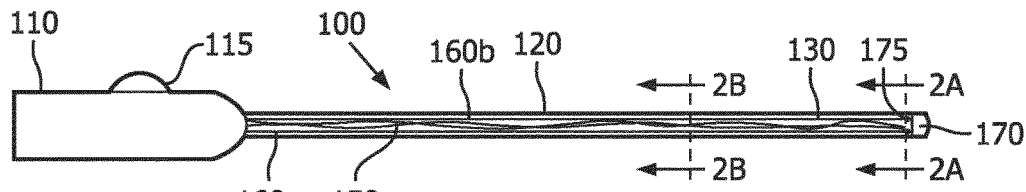
Figure 1C:
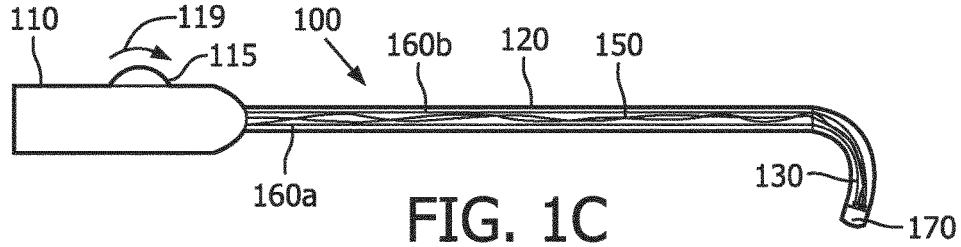

As in a conventional catheter as illustrated in FIG. 1, the transducer cables 150 are coupled to a transducer 170 at a flexible distal end 130 of the catheter, and to the handle 110 for coupling to a medical control device (not illustrated) in the handle 110 or external to the handle 110. The articulation pull-cables 160 are fixedly attached to a terminator 175 at the far end of the flexible distal end 130, and coupled to an articulation control element 115 in the handle 110. Depending upon the structure of the control element 115, the articulation pull-cables 160 may be fixedly attached to the control element 115, or moveably attached to the control element 115, such as a pair of articulation pull-cables 160 comprising a continuous cable on a perimeter of a wheel that is rotated by the control element 115, exerting tension on one articulation pull-cable of the pair and slackening the other articulation pull-cable. The insertion tube 120 is attached to the handle 110 and the flexible distal end 130.

Non limiting examples of the transducer 170 according to the present disclosure are an electromechanical transducer, an electroacoustic transducer such as an ultrasonic (or ultrasound) transducer.

The lumens 450, 460 provide isolation of the articulation pull-cables 160 from the transducer cables 150, and from each other. The pull-cable lumens 460 are sized to enable free travel of the articulation pull-cables 160. In embodiments of this invention, the articulation pull-cables 160 or the pull-cable lumen 460, or both, may be coated with a lubricous material that facilitates travel of the articulation pull-cable through the pull-cable lumen. In some embodiments, the insert comprises lubricous material to facilitate insertion of the insert into the insertion tube 420. In some embodiments, the insert comprises a high-temperature resilient material.

Figure 5:
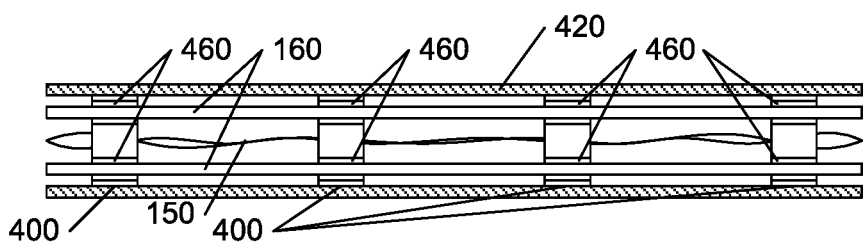
FIG. 5 illustrates a plurality of inserts in an insertion tube.

Although the insert 400 may extend the entire length of the insertion tube 420, such a structure is likely to interfere with the flexibility of the insertion tube 420. Accordingly, in embodiments of this invention, a plurality of inserts 400 are situated along the length of the insertion tube, as illustrated in FIG. 5. To prevent displacement or rotation of each insert, the inserts 400 may be attached to the insertion tube 420 using heat staking, RF welding, or other attachment techniques.

Figure 6:
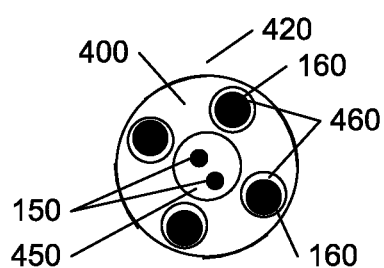
FIGS. 6 and 7 illustrate alternative insert structures.
Figure 7:
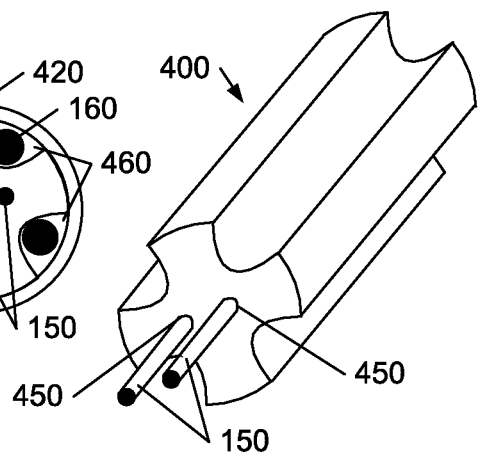

FIGS. 6 and 7 illustrate alternative structures for the insert 400. In FIG. 6, an enclosing pull-cable lumen 460 is provided for each articulation pull-cable 160, to facilitate assembly. In this embodiment, the transducer cables 150, the articulation pull-cables 160, and the inserts 400 can be pre-assembled as a string of components that are subsequently enclosed by the insertion tube 420, as detailed further below.

FIG. 7 illustrates an example embodiment wherein the transducer cables 150 are embedded in the insert 400. That is, each insert 400 is molded or otherwise formed around the transducer cables 150 such that the cables 150 are fixedly attached to each insert 400. In this embodiment, closed transducer-cable lumens 450 are formed by the cables 150 as each insert is formed.

Figures 8, 9:
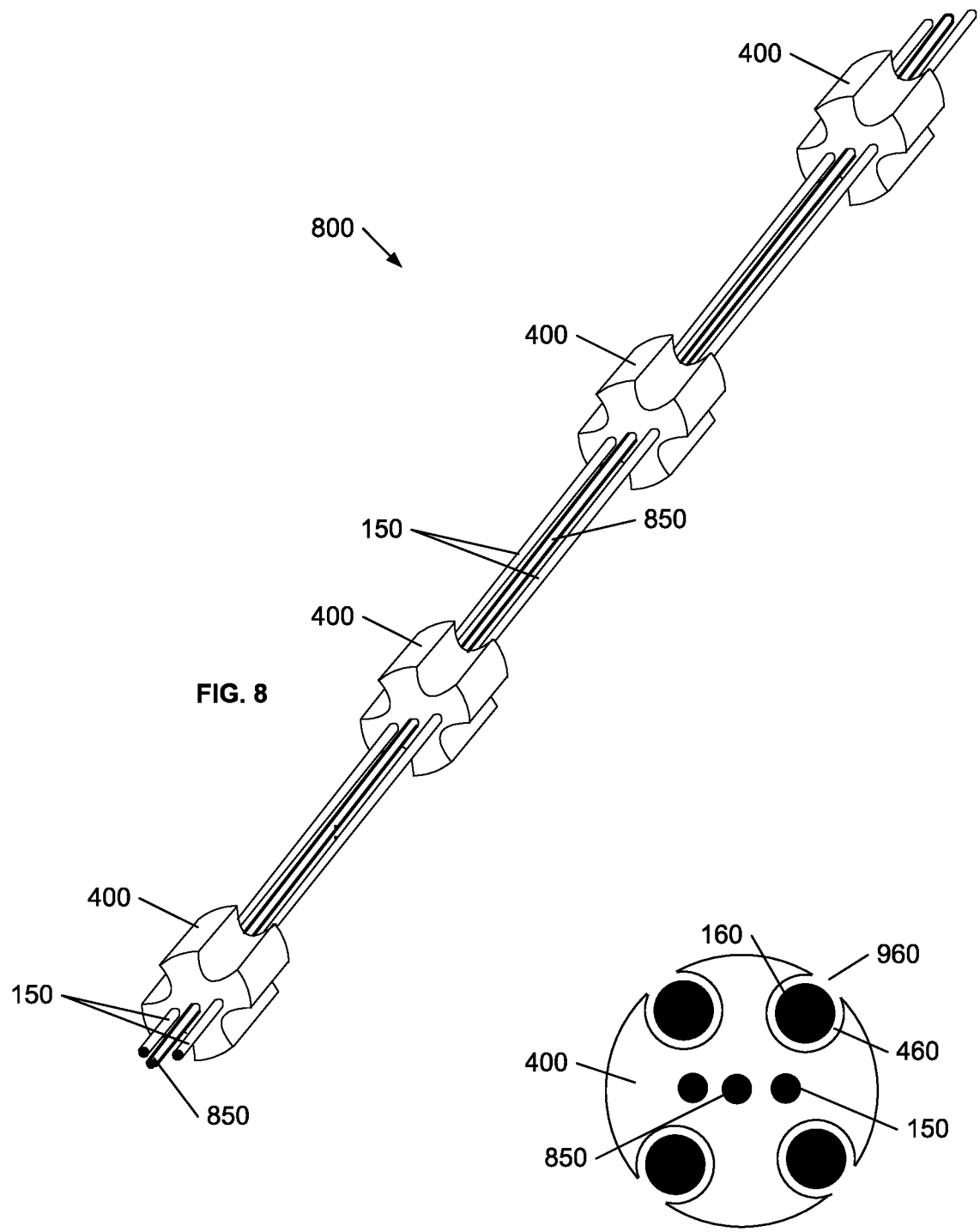
FIG. 8 illustrates a string of components for insertion into an insertion tube.
FIG. 9 illustrates an alternative insert structure.

FIG. 8 illustrates an example string of components 800 comprising the transducer cables 150 embedded in each of a plurality of inserts 400. Also embedded in each insert 400 is a draw wire 850. The draw wire 850 may be used to pull the string 800 through the insertion tube 420 to create the assembly illustrated in FIG. 5.

If the inserts 400 include enclosing pull-cable lumens 460 as illustrated in FIG. 6, the articulation pull-cables 160 may be strung through the pull-cable lumens 460 of this string of components 800. Alternatively, if the inserts 400 comprise open pull-cable lumens 460 as illustrated in FIG. 7, the articulation pull-cables 160 may be laid into each pull-cable lumen 460 of the inserts 400 as a string of components similar to the string of components 800 are drawn into the insertion tube 420.

FIG. 9 illustrates an example insert that is structured to capture each articulation pull-cable 160 as it is laid into the pull-cable lumen 460. As illustrated, the insert 400 includes a trough that has an opening 960 that is slightly smaller than the diameter of the articulation pull-cable 160. In this embodiment, the insert 400 comprises a resilient material that enables the larger articulation pull-cable 160 to be inserted through the smaller opening 960. Once inserted, the articulation pull-cable 160 is captured by the pull-cable lumen 460 within the pliable material as it returns to its original state of having a smaller opening 960 than the diameter of the articulation pull-cable 160.

Figure 10:
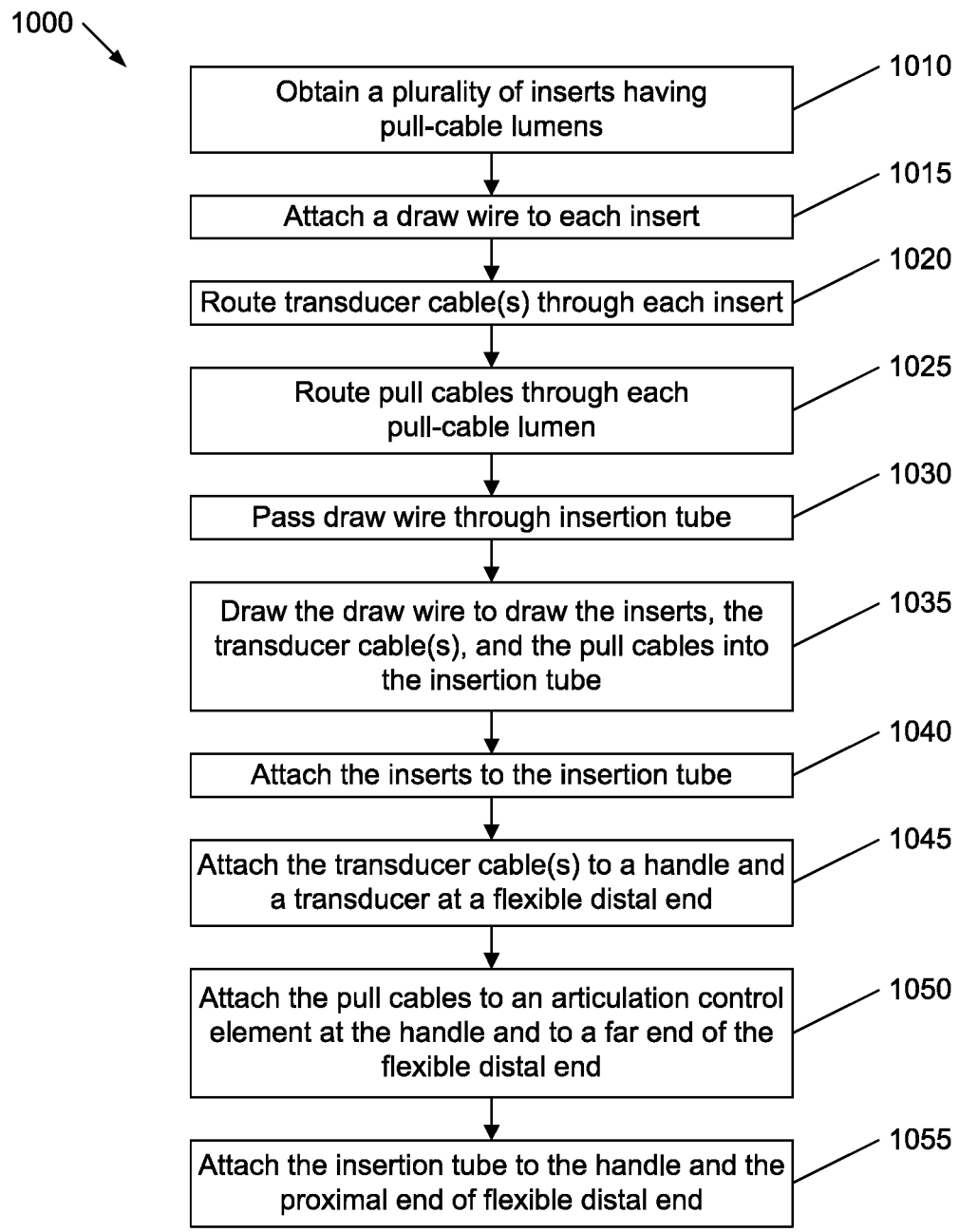
FIG. 10 illustrates an example flow diagram for assembling a steering catheter.

FIG. 10 illustrates an example flow diagram 1000 for assembling a steering catheter with articulation pull-cable support within the insertion tube. One of skill in the art will recognize that the illustrated order of steps is provided for ease of understanding, and the steps may be performed in different order, and/or some steps may be performed concurrently. One of skill in the art will also recognize that, with the exception of installing the inserts with articulation pull-cable and transducer cable lumens in the insertion tube, the assembly of the steering catheter is consistent with known prior art techniques that do not require detailed descriptions in this specification.

At 1010, a plurality of inserts having pull-cable lumens are obtained. These may be pre-formed inserts, or created by extrusion or molding about a draw wire and/or transducer cables. At 1015, a draw wire is attached to each insert, and at 1020, one or more transducer cables are routed through each insert. As noted above, steps 1010, 1015, and 1020 may be performed concurrently, as when the inserts are coextruded over the draw wire and the transducer cable(s).

At 1025, the articulation pull-cables are routed through the pull-cable lumens of each insert. If the pull-cable lumens are troughs, the articulation pull-cables may be temporarily held in place until the insert is about to be drawn into the insertion tube.

At 1030, the draw wire is passed through the insertion tube, and at 1035, the draw wire is drawn to draw the assembly of inserts, transducer cable(s), and articulation pull-cables into the insertion tube. In alternative embodiments, the insertion tube may be extruded or otherwise formed over the assembly, eliminating the need for a draw wire.

At 1040, the inserts are attached to the insertion tube. This attachment is optional; if the inserts are sufficiently held in place by elastic pressure from the walls of the insertion tube, or by the formation of the insertion tube upon the assembly, further attachment may be unnecessary. As noted above, if attachment is necessary, heat staking, RF welding, or other attachment techniques may be used. In some embodiments, the insertion tube may be a heat-shrink material that facilitates placement of the assembly in the insertion tube, and heat is subsequently applied to attach the insertion tube to each insert.

At 1045, the transducer cables are attached at each end to couple the transducer to the handle, and at 1050, the articulation pull-cables are attached at each end of the assembly so as to couple the flexible distal end to an articulation control in the handle.

Final assembly of the catheter is performed by coupling the insertion tube to the handle and the flexible distal end, at 1055.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein a continuous insert is coextruded over the transducer cables, then selectively etched or otherwise reduced in diameter to create a plurality of full-size (un-etched) inserts between these thinner (etched) segments. For example, the material between the pull-cable lumens 460 along the perimeter of the continuously extruded insert can be selectively removed, leaving only the transducer cables embedded in the residual material between the unmodified inserts.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Reference signs in the claims, if any, should not be construed as limiting the scope of the claims.

The invention claimed is:

1. An elongated medical device comprising:
a handle comprising a steering element;
a flexible distal end comprising a transducer;
at least one transducer cable configured to couple the handle to the transducer;
a plurality of articulation pull-cables configured to couple the steering element to the flexible distal end and to be controlled at the steering element so as to articulate the flexible distal end in a desired direction;
an insertion tube disposed between the handle and the flexible distal end;
a plurality of inserts configured to be spaced along the insertion tube from the handle to the flexible distal end, each insert of the plurality of inserts having a length and including a plurality of lumens comprising:
one or more transducer-cable lumens through which the at least one transducer cable extends,
a plurality of pull-cable lumens through which the plurality of articulation pull-cables extends, and
a draw wire lumen through which a draw wire extends, the draw wire lumen situated at a center area of the insert and extending the length of the insert; and
the draw wire configured to pass through the draw wire lumen of each insert and pull the plurality of inserts as a string of components into the insertion tube,
wherein the plurality of lumens isolate the at least one transducer cable and each of the plurality of articulation pull-cables from each other.

2. The device of claim 1, wherein a flexibility of the flexible distal end is substantially greater than a flexibility of the insertion tube.

3. The device of claim 1,
wherein each of the one or more transducer-cable lumens is situated in the center area of each insert, and
wherein each of the plurality of pull-cable lumens is situated along a perimeter area of each insert.

4. The device of claim 1, wherein each of the plurality of pull-cable lumens comprises a C-shaped lumen at a perimeter of a corresponding insert of the plurality of inserts.

5. The device of claim 4, wherein an opening in the C-shaped lumen is smaller than a diameter of an articulation pull-cable of the plurality of articulation pull-cables.

6. The device of claim 1, wherein the one or more transducer-cable lumens are closed and fixedly attached to the at least one transducer cable.

7. The device of claim 1, wherein each of the plurality of pull-cable lumens are sized to allow each articulation pull-cable to freely travel through the plurality of pull-cable lumens.

8. The device of claim 1, wherein each of the plurality of pull-cable lumens includes a lubricous material that facilitates travel of an articulation pull-cable of the plurality of articulation pull-cables through the pull-cable lumen.

9. The device of claim 1, wherein each insert comprises a high-temperature resilient material.

10. The device of claim 1, wherein each insert is secured to the insertion tube.

11. The device of claim 1, wherein the at least one transducer cable, the plurality of articulation pull-cables, and the plurality of inserts are arranged as the string of components that is inserted into the insertion tube.

* * * * *